(12) United States Patent
Huang et al.

(10) Patent No.: US 10,611,993 B2
(45) Date of Patent: Apr. 7, 2020

(54) MULTICHANNEL IN-VITRO METABOLISM REAL-TIME MONITORING APPARATUS

(71) Applicant: RAYCAN TECHNOLOGY CO., LTD. (SU ZHOU), Suzhou New District, Suzhou, Jiangsu (CN)

(72) Inventors: Gang Huang, Jiangsu (CN); Xiaoke Wu, Jiangsu (CN); Luyao Wang, Jiangsu (CN); Jun Zhu, Jiangsu (CN); Qingguo Xie, Jiangsu (CN)

(73) Assignee: Raycan Technology Co., Ltd. (Suzhou), Suzhou, Jiangsu (CN)

( * ) Notice: Subject to any disclaimer, the term of this patent is extended or adjusted under 35 U.S.C. 154(b) by 96 days.

(21) Appl. No.: 15/036,260

(22) PCT Filed: Feb. 27, 2014

(86) PCT No.: PCT/CN2014/072609
§ 371 (c)(1),
(2) Date: May 12, 2016

(87) PCT Pub. No.: WO2015/100849
PCT Pub. Date: Jul. 9, 2015

(65) Prior Publication Data
US 2016/0298075 A1   Oct. 13, 2016

(30) Foreign Application Priority Data
Dec. 30, 2013   (CN) .......................... 2013 1 0743216

(51) Int. Cl.
*C12M 1/34* (2006.01)
*C12M 1/00* (2006.01)
*C12M 1/24* (2006.01)

(52) U.S. Cl.
CPC ............ *C12M 41/46* (2013.01); *C12M 23/08* (2013.01); *C12M 29/10* (2013.01)

(58) Field of Classification Search
CPC ....... C12M 41/46; C12M 23/08; C12M 29/10
See application file for complete search history.

(56) References Cited

U.S. PATENT DOCUMENTS

| | | | |
|---|---|---|---|
| 4,967,084 A * | 10/1990 | Rich | G01T 1/172 250/361 R |
| 2010/0029000 A1 | 2/2010 | Zhong et al. | |
| 2013/0316442 A1 | 11/2013 | Meurville et al. | |

FOREIGN PATENT DOCUMENTS

| CN | 101270332 A | 9/2008 |
|---|---|---|
| CN | 201501875 U | 6/2010 |

(Continued)

OTHER PUBLICATIONS

Machine Translation of CN201501875, Accessed Feb. 2, 2018 (Year: 2018).*

(Continued)

*Primary Examiner* — William H. Beisner
*Assistant Examiner* — Danielle B Henkel
(74) *Attorney, Agent, or Firm* — Knobbe, Martens, Olson & Bear, LLP (57) ABSTRACT

A multichannel in-vitro metabolism real-time monitoring apparatus includes a radiation probing apparatus and a constant flow culture apparatus. The constant flow culture apparatus includes a liquid supply bottle, a waste liquid bottle, a multichannel infusion apparatus, and a multichannel liquid separation apparatus. The radiation probing apparatus has two groups of probing modules with flat structures, which are separately disposed on two sides of multichannel biochemical culture apparatuses and are used for recording radiation activities in the multichannel biochemical culture apparatuses in real time.

18 Claims, 2 Drawing Sheets

(56) References Cited

FOREIGN PATENT DOCUMENTS

| CN | 202450092 U | 9/2012 |
|----|-------------|--------|
| CN | 102879798 A | 1/2013 |
| CN | 103347996 A | 10/2013 |

OTHER PUBLICATIONS

Machine Translation of CN202450092, Accessed Feb. 2, 2018 (Year: 2018).*
1st Chinese Office Action dated May 3, 2016 for Application No. 201310743216.2 in 16 pages (translation included).
2nd Chinese Office Action dated Jan. 17, 2017 for Application No. 201310743216.2 in 17 pages (translation included).

* cited by examiner

MULTICHANNEL IN-VITRO METABOLISM REAL-TIME MONITORING APPARATUS

This application is the U.S. National Phase under 35. U.S.C. § 371 of International Application PCT/CN2014/072609, filed Feb. 27, 2014, which claims priority to Chinese Patent Application No. 201310743216.2, entitled "MULTICHANNEL IN-VITRO METABOLISM REAL-TIME MONITORING APPARATUS", filed with the Chinese State Intellectual Property Office on Dec. 30, 2013, which is incorporated by reference in its entirety herein.

FIELD

The disclosure relates to the field of radiation detection and biomedical metabolism analysis, and in particular to a multichannel in-vitro metabolism real-time monitoring apparatus based on a real-time coincidence detection and a continuous cultivation.

BACKGROUND

Currently, in fields such as biology and medicine, in order to study characteristics of biological behaviors related to organisms such as cells, tissue and organs, for example, uptake of organism metabolite such as glucose, amino acids and fatty acids, a detecting scheme is widely adopted. The detecting scheme includes: in-vitro cultivating living biological tissue by adding the above metabolites with a radioactive nuclide label into a biochemical cultivating instrument; and detecting radioactivity distribution information of a sample by a radiation detector, to reflect the number of labels taken by the sample. Compared with another conventional scheme for detecting an in-vitro tissue physiological activity based on fluorescence imaging, the above scheme has the following advantages: since imaging methods such as PET and SPECT which use a same label and a same monitoring means may be adopted in clinic, a conclusion obtained with an in-vitro experiment can be used to guide an in-vivo experiment better, and the in-vitro experiment and the in-vivo experiment can be cross-checked with each other.

For example, in one of important methods for oncology research, different medicines are added into a tumor cell strain cultivated in-vitro, and an impact on a biochemical activity by the medicines is observed to evaluate the curative effect of the medicines. A rate at which a tumor cell makes an uptake of metabolite, especially glucose, is closely related to a biological activity of the tumor cell, which is represented as related to sensitivity on medicine of the tumor in dine. For researching a physiological mechanism of the tumor and evaluating a medicine, it is critical to monitor, based on the in-vitro experiment and the in-vivo experiment, a process in which a tumor cell makes an uptake of glucose. For a same administration individual, the biochemical activity in a level of cell and tissue is researched by in-vitro cultivating and monitoring the tissue of a body, and a biological research in a level of organ and organism is completed with an in-vivo imaging, thereby achieving a multilevel evaluation of medicine effect under a same receptor source, a same monitoring means and a same evaluation system, and realizing an individual medical treatment truly.

In one of the current methods for quantitatively monitoring an in-vitro metabolism process includes: after multiple batches of same tumor cell strains are cultivated in a cultivating dish and the glucose with the radioactive nuclide label or the like, such as 18F-FluoroDeoxyGlucose (18F-FDG) solution, is added into the cultivating dish, the tumor cell strains are incubated in a cell incubator box. Then, cells of different batches are collected at several time points, cultivating solution is cleaned and the collected cells are placed in a fully enclosed gamma counter to monitor left radiation doses in the respective cells, thereby calculating the amount of the glucose taken by the tumor cell strain at different time points[1][2].

In the above scheme with the static cultivating device and the fully enclosed gamma counter, substantially, multiple sampling points in time are obtained by increasing the number of the same disposable samples. An apparent disadvantage of the above scheme is that, only information of metabolite cumulative doses at several discrete time points can be obtained and it is difficult to measure an uptake rate of the tissue dynamically and continuously, hence the obtained information can not reflect a full view of a biochemical process. Since only one sample can be monitored in the fully enclosed gamma counter once and the cultivating solution needs to be cleaned to leave only adherent cells before the sample is monitored, the sample can not be reused after the sample is monitored. In this case, a large number of samples need to be incubated to obtain more accurate activity-time information, and in a monitoring, it is required to try to operate a same batch of samples simultaneously to ensure a conform sample test condition. In short, if the above scheme is adopted to perform a continuous monitoring, an experiment cost and an operation complexity are unbearable, a radiation harm suffered by an operator is increased hundredfold as compared with a single experiment, and an error is more easily caused by manual operations in multiple times and differences between samples of different batches.

In another scheme for quantitatively monitoring the in-vitro metabolism process, a detecting is performed with a Positron Emission Tomography (Positron Emission Tomography, hereinafter referred to as PET) imager [1]. The PET instrument may rebuild an image reflecting a distribution of radioactivity in an imaging region by detecting position information of a couple of gamma photons generated in a positron decay of radioactive nuclide. A cultivating dish containing radioactive metabolites is placed in a PET detector ring and is imaged. Since a light and a shade in a PET image represent different radioactivity, activity information may be obtained by calculating a sum of pixel values inside a cultivating well.

In the scheme using the PET, a sensitivity issue needs to be addressed firstly. An imaged object of the PET instrument is a human body or an animal, hence a structure of a detector of the PET instrument is annular and a ring gauge is generally tens of centimeters. In this case, a detecting angle is small for a cultivating dish with a flat-plate structure, and a detecting sensitivity is low. In addition, the PET instrument is used to performing an imaging, the number of cells cultivated in-vitro is small ($10^5 \sim 10^6$ per cultivating well) and the number of injected radioactive labels is small ($10 \sim 10^4$ Bq). In this case, it is difficult to achieve a real-time monitoring due to a prolonged imaging time for acquiring sufficient imaging data and a time consumption for image rebuilding and processing. Since a spatial resolution of the PET instrument is generally several millimeters, a capability for distinguishing radioactive events from different cultivating wells is limited. Finally, since a capacity of the PET instrument is large and it is expensive to buy and maintain the PET instrument, the PET instrument is not suitable to serve as an analysis tool for in-vitro metabolism level research.

In another common method for quantitatively monitoring the in-vitro metabolism process, a gamma camera is adopted [2]. A basic structure of the gamma camera is the same as that of a single PET detecting module, but a collimator needs to be mounted in front of a scintillation crystal, to prevent a gamma ray in a non-specified range and a non-specified direction from entering the crystal, hence information is acquired orientedly. When being used, the gamma camera is placed directly above a detected object. Gamma rays filtered by the collimator are detected through the scintillation crystal, a photoelectric conversion component and a back-end electronics, and position information of the gamma rays is calculated. After the data is acquired, a two-dimension projection image representing a radioactivity distribution of the detected object may be obtained based on a distribution of incident positions of the gamma rays.

In the scheme using the gamma camera, a sensitivity issue still needs to be addressed. Since the collimator is needed in the gamma camera, the detector can not be against the detected object. In this case, a detecting angle is small and a sensitivity is small (about 1% for a single cultivating well), and it takes a long acquisition time to acquire one frame of image. Therefore, it is difficult to achieve a real-time monitoring. In addition, an existence of the collimator and a calculation of position information degrade the spatial resolution of the detector [3][4]. In this case, a source of gamma photon can not be calculated accurately, and errors may exist in the final-obtained radioactivity count for cultivating positions.

Furthermore, experiment designs in cell and molecule levels tend to be high-throughput, that is, large numbers of samples are monitored in one experiment. Therefore, a multichannel cultivating instrument such as a multiwell cell cultivating plate is generally adopted. The multiwell cell cultivating plate is formed by arranging multiple cultivating dishes with a same specification on a same plate in array, and is widely used as a cultivating instrument in a biochemical field due to its high integration level, standardization and operational convenience. However, in the above three detecting methods, the fully enclosed gamma counter can only monitor one sample once, and can not monitor multiple cultivating dishes distinguishingly. The PET and the gamma camera can not distinguish counts for adjacent regions in two cultivating channels accurately, have different detecting sensitivities for different cultivating channels, and thus are not suitable to serve as a monitoring apparatus in a high-throughput experiment.

Therefore, for the above technical issues, a new multichannel in-vitro metabolism real-time monitoring apparatus needs to be provided to overcome the above defects.

[1] Fischer B M, Olsen M W B, Ley C D, et al. How few cancer cells can be detected by positron emission tomography? A frequent question addressed by an in vitro study[J]. European journal of nuclear medicine and molecular imaging, 2006, 33(6): 697-702.

[2] Zinn K R, Chaudhuri T R, Buchsbaum D J, et al. Detection and measurement of in vitro gene transfer by gamma camera imaging[J]. Gene therapy, 2001, 8(4): 291-299.

[3] Scopinaro F, Pani R, De Vincentis et al. High-resolution scintimammography improves the accuracy of technetium-99m methoxyisobutylisonitrile scintimammography: use of a new dedicated gamma camera[J]. European journal of nuclear medicine, 1999, 26(10): 1279-1288.

[4] Xiaohua Li, Ruzhen Gao, Fuxiang Liu. Influence of detect distance on space resolution of γ camera system[J]. Chinese Medical Equipment Journal, 1990, 03: 6-8.

SUMMARY

In view of the above, the present disclosure provides a multichannel in-vitro metabolism real-time monitoring apparatus, with which distribution information of radioactivity for multiple cultivating channels can be acquired and displayed in real-time, a curve of metabolite uptake during a whole experiment may be obtained, it is reflected more completely an impact on target biological tissue by a parameter to be researched and a high-throughput experiment is achieved.

In order to achieve the above objective, the present disclosure provides the following technical schemes.

A multichannel in-vitro metabolism real-time monitoring apparatus for continuously cultivating in-vitro biological samples in multiple channels and monitoring metabolism information of the in-vitro biological sample in each of the multiple channels, includes a constant flow cultivating device and a radiation detecting device, where the constant flow cultivating device is configured to continuously cultivate biological samples in multiple channels of a multichannel biochemical cultivating instrument; and the radiation detecting device is configured to monitor radioactivity for each of the multiple channels in real time.

Preferably, in the above multichannel in-vitro metabolism real-time monitoring apparatus, the constant flow cultivating device may include a solution supply flask, a multichannel constant flow infusing unit and a multichannel solution separating unit, where the solution supply flask may be configured to provide fresh cultivating solution containing a radioactive label;

the multichannel constant flow infusing unit may be configured to input and output cultivating solution containing a radioactive metabolic substrate to and from each of the multiple channels of the multichannel biochemical cultivating instrument, to provide updated cultivating solution with a constant flow rate to a cultivated object; and the multichannel solution separating unit may be configured to equally distribute the cultivating solution to each of cultivating wells and collect waste solution from each of the cultivating wells with independent channels.

It can be seen from the above technical schemes that, in the present disclosure, with a constant flow cultivating scheme, a full-automation of cultivating in-vitro tissue in a long-term is achieved and the distribution information of the radioactivity for the multiple cultivating channels is acquired and displayed in real time, thereby acquiring metabolism changing information more really and entirely. Moreover, a coincidence detection is achieved with a detecting module having an open flat-plate structure. In this case, standard biochemical multiwell cultivating instruments may be adopted to perform experiments for multiple channels in parallel. Experiments for multiple groups and multiple samples may be performed simultaneously, thereby improving an experiment throughput, an efficiency and bring a good condition consistency between groups.

Compared with the conventional technologies, the present disclosure has the following advantages.

(1) With a constant flow cultivating scheme, an automation of cultivating in-vitro tissue in long-term is achieved and the distribution information of the radioactivity can be acquired and displayed in real time. In this case, an in-vitro metabolism process can be monitored in real time for a long period, data objects for an in-vitro metabolism research forms a continuous and real-time curve instead of several discrete points, thereby acquiring metabolism changing information more really and entirely.

(2) A coincidence detection scheme is performed on gamma photons generated from a decay of radioactive labels, by using a couple of detecting modules with open flat-plate structures. In this case, radioactivity for different cultivating channels on a same plane can be distinguished accurately and standard biochemical multiwell cultivating instruments may be adopted to perform experiments for multiple channels in parallel, which has advantages such as high-throughput, high sensitivity and good condition consistency between groups.

(3) A non-invasive coincidence detection scheme is adopted. In this case, an open detector structure is allowed, a normal metabolism process of a detected sample is never destroyed and the sample can be reused. Therefore, it is unnecessary to cultivate large numbers of different batches of samples as in the existing monitoring methods.

(4) Since a continuous constant flow cultivating scheme and a real-time detecting scheme are adopted and the experiment is performed fully automatically, an operator may operate remotely far away from a radiation source.

(5) A coincidence detection scheme is adopted. Sensitivity for different regions in a view field can be adjusted by adjusting a relative position of a detector or a cultivating dish. And different weights of sensitivity is given to the cultivating solution in an upper layer and cultivating cells in a lower layer, because the number of the radioactive labels taken by a cell in the lower layer is a focus of the experiment. In this way, a measuring result can be more accurate and apparent.

(6) A general cultivating instrument in the biomedical field is adopted as a carrier for an experiment object, which is convenient to be used by being coupled with other biochemical analysis instruments.

BRIEF DESCRIPTION OF THE DRAWINGS

The drawings to be used in the description of the embodiments or the conventional technology will be described briefly as follows, so that the technical schemes according to the embodiments of the present disclosure or according to the conventional technology will become clearer. It is apparent that the drawings related to the present disclosure in the following description only illustrate some embodiments of the present disclosure. For those skilled in the art, other drawings may be obtained according to these drawings without any creative work.

DETAILED DESCRIPTION OF EMBODIMENTS

The present disclosure provides a multichannel in-vitro metabolism real-time monitoring apparatus, with which distribution information of radioactivity for multiple cultivating channels can be acquired and displayed in real time and a curve of uptake metabolite during a whole experiment may be obtained, thereby more completely reflecting an impact on target biological tissue by a parameter to be researched and achieving a high-throughput experiment.

The multichannel in-vitro metabolism real-time monitoring apparatus according to the present disclosure is configured to continuously cultivate in-vitro biological samples in multiple channels and monitor metabolism information of the in-vitro biological sample in each of the multiple channels, the multichannel in-vitro metabolism real-time monitoring apparatus includes a constant flow cultivating device and a radiation detecting device, where the constant flow cultivating device is configured to continuously cultivate biological samples in multiple channels of a multichannel biochemical cultivating instrument; and the radiation detecting device is configured to monitor radioactivity for each of the multiple channels in real time.

Figure 1:
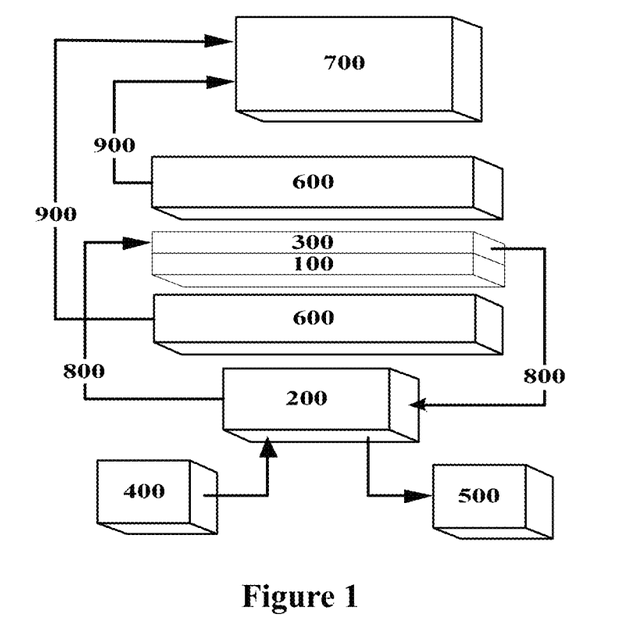
FIG. 1 is a schematic diagram of connections between a constant flow cultivating device, a radiation detecting device and a multichannel biochemical cultivating instrument in a multichannel in-vitro metabolism real-time monitoring apparatus according to the present disclosure.

As shown in FIG. 1, the constant flow cultivating device includes a solution supply flask 400, a waste solution flask 500, a multichannel constant flow infusing unit 200 and a multichannel solution separating unit 300, where the solution supply flask 400 is configured to provide fresh cultivating solution containing a radioactive label;

the waste solution flask 500 is configured to collect the cultivating solution refluxed from the multichannel biochemical cultivating instrument 100 after tissue in the multichannel biochemical cultivating instrument 100 is cultivated and metabolized;

the multichannel constant flow infusing unit 200 is configured to input and output cultivating solution containing a radioactive metabolic substrate to and from each of the multiple channels of the multichannel biochemical cultivating instrument 100, to provide updated cultivating solution with a constant flow rate to a cultivated object; and the multichannel solution separating unit 300 is configured to equally distribute the cultivating solution to each of cultivating wells and collect waste solution from each of the cultivating wells with independent channels.

The multichannel constant flow infusing unit 200 is a constant flow bump.

Figure 2:
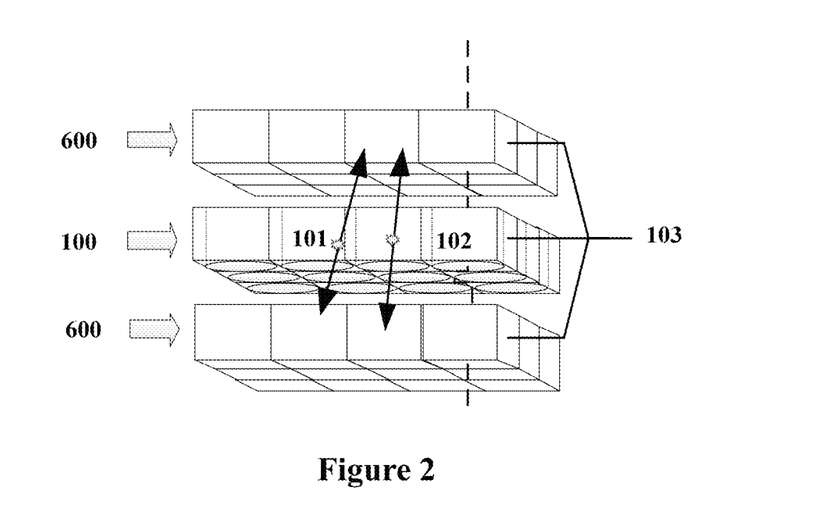
FIG. 2 is a schematic diagram of positions of a radiation detecting device and a 12-well multichannel biochemical cultivating instrument according to the present disclosure.

As shown in FIGS. 1 and 2, the radiation detecting device includes two detecting modules 600 respectively arranged on two sides of the multichannel biochemical cultivating instrument 100, each of the two detecting modules 600 has a flat-plate structure. The two detecting modules 600 are configured to perform a coincidence detection on the multichannel biochemical cultivating instrument 100, record the radioactivity for each of cultivating wells of the multichannel biochemical cultivating instrument 100 in real time and continuously monitor a total number of metabolic substrates in each of the cultivating wells. The two detecting modules 600 are completely the same and are opposite to each other.

Each of the two detecting modules 600 includes multiple dedicated detecting units corresponding to the cultivating wells in a one-to-one manner, and the dedicated detecting unit is changed based on different cultivating well specifications.

A center of the detecting unit is aligned with a center of a circle of the cultivating well corresponding to the detecting unit, and a length of a side of the detecting unit is equal to a diameter of the cultivating well corresponding to the detecting unit.

Besides the above dedicated detecting units, of course, non-dedicated detecting units may be adopted. That is, each of the two detecting modules may include multiple non-dedicated detecting units with constant sizes, the non-dedicated detecting unit with the constant size is formed by constant array detectors which are combined into a detecting unit with a same size as a used cultivating well in a subsequent data processing procedure.

The multichannel biochemical cultivating instrument is a general instrument for in-vitro cultivation in the biomedical field, and has multiple specifications such as 6-well, 12-well, 24-well, 48-well and 96-well based on different numbers of wells, with size parameters of the specifications being constant.

In summary, the detecting module according to the present disclosure may be a dedicated probe of which the detecting units corresponds to the cultivating wells in a one-to-one manner, and the probe may be changed based on different cultivating well specifications. Alternatively, the detecting module may be formed by constant fine array detectors which are combined into the detecting unit with a same size as the used cultivating well in the subsequent data processing procedure. The detecting principles of the above two schemes are consistent, and both meet a condition that the cultivating well corresponding to a couple of detecting units, which are respectively in the two detecting modules and located at positions corresponding to each other, is located just and only between the couple of detecting units. A 12-well circular multichannel biochemical cultivating instrument 100 in FIG. 2 of the present disclosure is only for exemplary descriptions, and the shapes and the number of the cultivating wells are not limited in the principle of the present disclosure.

The multichannel in-vitro metabolism real-time monitoring apparatus includes a position adjusting device configured to adjust relative positions between the two detecting modules and the multichannel biochemical cultivating instrument.

Figure 3:
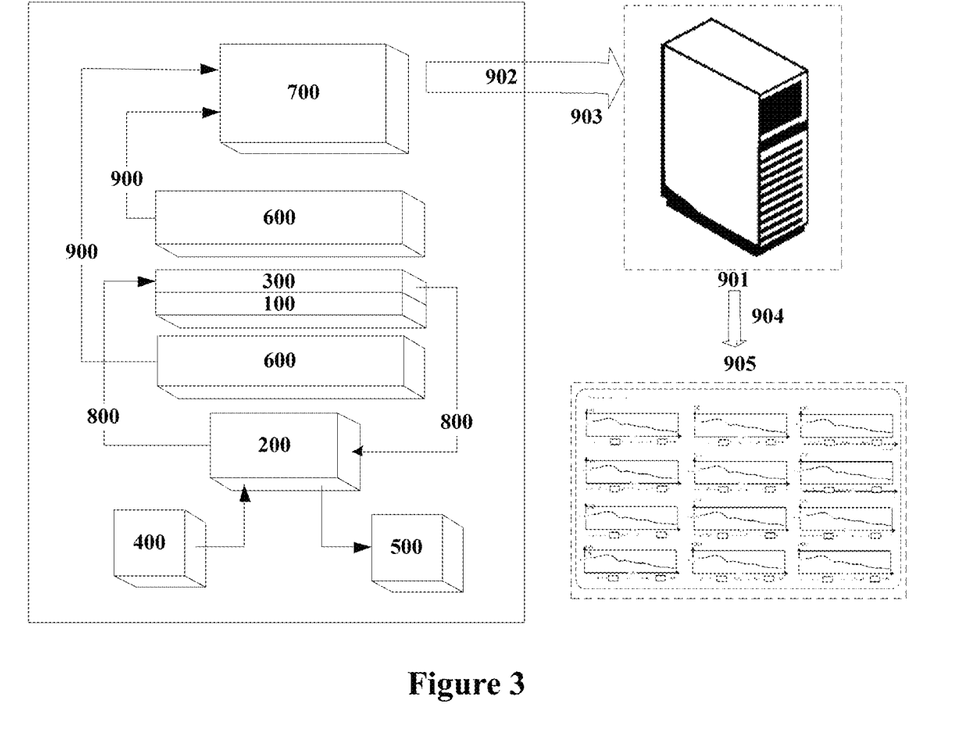
FIG. 3 is a system block diagram of a multichannel in-vitro metabolism real-time monitoring apparatus according to the present disclosure.

As shown in FIG. 3, the multichannel in-vitro metabolism real-time monitoring apparatus further includes a data processing transmitting module 700 connected to the radiation detecting device, where the data processing transmitting module 700 is configured to package acquired detecting information into a single event data frame and transmit the single event data frame to a host computer 901, to process and analyze the single event data frame with analysis software on the host computer.

In FIG. 1, 800 represents the cultivating solution containing a radioactive label and 900 represents data of a single gamma photon.

In FIG. 2, 101 represents rejection, 102 represents acception, and 103 represents that each cultivating well corresponds to a couple of detecting units consisting of a detecting unit above the cultivating well and a detecting unit below the cultivating well.

In FIG. 3, 902 represents an information data package of a single gamma photon, 903 represents a transmission manner, 904 represents a coincidence count and 905 represents a radioactivity-time curve of a cultivating unit.

The analysis software is configured to: perform in real time a position coincidence and a time coincidence on a single gamma photon data frame received from two detecting modules 600 with flat-plate structures, to obtain count information of a decay event for each of the multiple channels of the multichannel biochemical cultivating instrument, to further obtain a time-count rate curve for each of the multiple channels and to complete a data processing analyzing function.

The multichannel biochemical cultivating instrument is a standardized instrument in a biomedical field.

The multiple channels of the multichannel biochemical cultivating instrument have a same specification, flow rates of cultivating solution respectively inputted to the multiple channels are the same and concentrations of radioactive metabolic substrates in the cultivating solution respectively inputted to the multiple channels are the same.

The object of the present disclosure is to monitor parallelly and in real time metabolism processes of multiple in-vitro cultivated biological samples. The principle of the present disclosure is described as follows. A multichannel constant flow infusing unit is adopted to input and output cultivating solution containing a radioactive metabolic substrate to and from each of the multiple channels of the multichannel biochemical cultivating instrument. Flow rates of the cultivating solution respectively inputted to the multiple channels are the same and concentrations of the radioactive metabolic substrates in the cultivating solution respectively inputted to the multiple channels are the same. Flow rates of cultivating solution respectively outputted from the multiple channels are the same, and the concentration of the radioactive metabolic substrate in the cultivating solution outputted from the channel depends on an uptake degree of the radioactive metabolic substrate after the radioactive metabolic substrate participates in the metabolism of the tissue in the cultivating instrument. Therefore, a total number of the radioactive metabolic substrates in the cultivating instrument depends on the number of the radioactive metabolic substrates taken by the tissue. The detecting modules with flat-plate structures (i.e. radiation detector array) arranged on the two sides of the cultivating instrument record the radioactivity for the cultivating instrument and monitor information of the total number of the metabolic substrates in the cultivating instrument in real time. In a cultivation process, a medicine to be researched is injected into an experiment group, the medicine may affect the number of the metabolic substrates taken by the cultivated biological tissue, which is reflected in the radioactivity for the cultivating instrument corresponding to the cultivated biological tissue in real time. By comparing relative change between curves of radioactivity counts for the experiment group and a reference group or curves of the radioactivity counts for different experiment groups, it may be determined whether the medicine promotes or restrains the metabolism or it may be obtained difference among effects of different medicines. A mathematical analysis tool may be further introduced to perform a deep research, such as a data fitting and a quantitative analysis, on acquired real-time count rate curves.

An implementation basic of the continuous real-time monitoring is the constant flow cultivating device. The constant flow cultivating device can input and output the cultivating solution with a constant flow rate to and from a cultivated object, thereby maintaining a constant solution amount while updating the solution in the cultivating device continuously. The above function of the constant flow cultivating device is an essential condition for long-term in-vitro tissue cultivation and an implementation premise of a detection principle in which uptake information is acquired by using differences between the concentration of an input radioactive metabolic substrate and the concentration of an output radioactive metabolic substrate. Since a couple of detectors with the flat-plate structures are used to perform a coincidence detection on a cultivating device between the couple of detectors, a radioactive dose in the cultivating device may be monitored continuously in real time.

An implementation basic of multichannel monitoring is an open structure of the plate detector and an application of a coincidence detection principle. It is possible to use a standardized multichannel biochemical cultivating instrument (i.e. a twelve-well cultivating plate) as a cultivating carrier due to the open structure of the plate detector. And in the coincidence detection principle, since a principle of emission directions of a couple of gamma photons generated due to a positron nuclide decay being reverse is used, gamma photons emitted from different cultivating wells may be counted through a time coincidence and a position coincidence. Once the cultivating device is placed in a plate detecting region, a continuous cultivation and a continuous monitoring are started. No manual operation is needed in the experiment process, thereby meeting requirements such as multiple channels, non-invasion and full-automation.

A detection principle of the radiation detecting device is described as follows. A detecting module included in the radiation detecting device includes a scintillation crystal, a photoelectric conversion component and a data processing transmitting module. In a case that gamma photons emitted from radioactive labels in the multichannel biochemical cultivating instrument enter the scintillation crystal, energy may be deposited and large numbers of visible light photons may be generated in the scintillation crystal. Next, the visible light photons are detected and converted into flashing pulse electrical signals by the photoelectric conversion component. And then, the data processing transmitting module acquires information of the gamma photons about time, position and energy, packages the acquired information into a single event data frame, and transmits the single event data frame to a computer via the Ethernet for subsequent processing and analysis.

As shown in FIG. 2, the 12-well multichannel biochemical cultivating instrument is taken as an example. In FIG. 2, two rectangular solid structures on two sides represent plate detecting modules completely the same and opposite to each other, and a rectangular solid structure in the middle represents a general standardized 12-well multichannel biochemical cultivating instrument for biochemical cultivation. The 12 wells are arranged in a 3*4 array. The plate detecting module is formed by arranging 12 square detecting units in a 3*4 array. A center of the detecting unit is aligned with a center of a circle of the cultivating well corresponding to the detecting unit, and a length of a side of the detecting unit is equal to a diameter of the cultivating well corresponding to the detecting unit. That is to say, it is ensured that the cultivating well is just interior tangent with a plane formed by connecting a group of sides of the detecting units corresponding to the cultivating well. In a case that a radionuclide tracer in the multichannel biochemical cultivating instrument decays, a couple of gamma photons emission directions of which are reverse are generated and the couple of gamma photons may be emitted in an arbitrarily angle. If and only if a couple of upper and lower detecting units opposite to each other both receive the gamma photons, it is considered that one decay is counted from the multichannel biochemical cultivating instrument corresponding to the couple of detecting units. If at least one of the couple of detecting units does not receive the gamma photons, it is considered that the decay is occurred in the cultivating well different from the cultivating well corresponding to the couple of detecting units, and the decay is not counted. Detecting sensitivities of the cultivating wells are the same since they correspond to the same detecting structure.

In the present disclosure, the radioactivity of the sample is calculated with a coincidence detection mode instead of the traditional single event detecting mode. In the coincidence detection, an open plate detecting structure may be adopted to distinguishingly detect multiple cultivating channels in the detecting range, thereby achieving a high-throughput in-vitro metabolism monitoring with a standardized multichannel biochemical cultivating instrument.

In the present disclosure, a constant flow cultivating mode is adopted, in which a same sample is cultivated continuously and can be monitored continuously in real time. In this case, it is unnecessary to cultivate large numbers of disposable samples for acquiring multiple sampling points.

The standardized cultivating instrument according to the present disclosure may be a general biochemical cultivating instrument with 6-well, 12-well, 24-well, 48-well, 96-well and the like, in addition to the 12-well plate shown in the figure.

In the present disclosure, an arriving time of a flashing pulse may be calculated with multiple time calculation methods such as ADC, MVT and CFD.

In the present disclosure, the multichannel constant flow infusing unit may be implemented as a bump, or a push syringe constant flow device, that is, technical means capable of providing continuous and constant solution flow rate each can be used to implement the multichannel constant flow infusing unit.

In the present disclosure, data may be transmitted between the radiation detecting device and a host computer via general data transmission schemes such as optical fiber, bus, serial port, USB port, Bluetooth, wifi, zigbee or the like.

In a method for distinguishingly counting the radioactivity for different cultivating positions according to the present disclosure, an occurring position of an annihilation event corresponding to a couple of gamma photons may be determined based on time flight information and position information of the couple of gamma photons, thereby determining a cultivating position corresponding to the annihilation event, and the number of the annihilation events corresponding to each of the cultivating positions is calculated to calculate activity information for different cultivating positions (method 1). Alternatively, after the cultivating instrument is imaged dynamically by a couple of plate detectors, a region division is performed on the image and the activity information for the cultivating position may be calculated by calculating a sum of pixel values corresponding to the cultivating position (method 2).

Implementations of the methods are described as follows.

In the method 1, a principle of emission directions of a couple of gamma photons generated simultaneously in a decay being reverse is used, a position point on a detector at which each of the gamma photons enters is acquired, thereby acquiring a connection line. A position on the connection line at which the decay event occurs may be determined based on information of a difference between times at which the two gamma photons arrive at the detectors. In this case, an actual position at which the decay event occurs in a detecting region is acquired. Such process is performed for each decay event, the activity information for different cultivating positions may be obtained finally.

A principle of the method 2 is the same as a principle of PET. That is to say, the couple of plate detectors serve as front detectors of the PET. A light and a shade in an acquired image represent the activity information for a region corresponding to the light and the shade. The acquired image are divided into regions based on a geometric size and a spatial position of a multichannel biochemical cultivating instrument, and the activity information for the region may be obtained by calculating a sum of pixel values in the region.

In the present disclosure, the scintillation crystal performing the radiation detection may be a crystal without background radiation, such as BGO and NaI, and the photoelectric component may be SiPM, APD, PMT, CCD and the like.

The multichannel in-vitro metabolism real-time monitoring apparatus according to the present disclosure is intended to reform a research means of in-vitro pharmacokinetics. The anteriority method in which the biochemical metabolism process is only "imaged as pictures" is improved into a real-time monitoring method in which the biochemical metabolism process is "recorded as a video". In this case, a curve showing metabolite uptake in a whole experiment may be obtained, thereby more completely reflecting an impact on the target biological tissue by a parameter to be researched. Moreover, compared with several discrete data points, it is more easily to perform deep and multiple data analysis on a continuous curve. In addition, the multichannel in-vitro metabolism real-time monitoring apparatus according to the present disclosure has advantages such as a high sensitivity, multiple channels, full-automation and a highly consistent experiment condition between groups, thereby being convenient to perform an experiment of microscale, high-throughput and multiple comparison.

In order to achieve the above objects, in the present disclosure, in-vitro tissue in multiple channels is cultivated in long-term automatically with a constant flow cultivating scheme, based on which distribution information of radioactivity for the multiple cultivating channels is acquired and displayed in real time. Moreover, a coincidence detection is performed with a detecting module having open flat-plate structure. The radioactivity for different cultivating channels may be counted distinguishingly. That is, radioactivity of an experiment object is detected with high-sensitivity and the activity counts for different regions are distinguished with the coincidence detection. In this case, a standardized biochemical multi-well cultivating instrument may be adopted to perform an in-vitro metabolism real-time monitoring experiment with high-throughput, microscale and a highly consistent experiment condition between groups, thereby acquiring and displaying the distribution information of the radioactivity in real time, and reflecting a realer and more entire metabolism changing information of the experiment object.

Compared with the conventional technologies, the present disclosure has the following advantages.

(1) With a constant flow cultivating scheme, an automation of cultivating in-vitro tissue in long-term is achieved and the distribution information of the radioactivity can be acquired and displayed in real time. In this case, an in-vitro metabolism process can be monitored in real time for a long period, data objects for an in-vitro metabolism research forms a continuous and real-time curve instead of several discrete points, thereby acquiring metabolism changing information more really and entirely.

(2) A coincidence detection scheme is performed on gamma photons generated from a decay of radioactive labels, by using a couple of detecting modules with open flat-plate structures. In this case, radioactivity for different cultivating channels on a same plane can be distinguished accurately and standard biochemical multiwell cultivating instruments may be adopted to perform experiments for multiple channels in parallel, which has advantages such as high-throughput, high sensitivity and good condition consistency between groups.

(3) A non-invasive coincidence detection scheme is adopted. In this case, an open detector structure is allowed, a normal metabolism process of a detected sample is never destroyed and the sample can be reused. Therefore, it is unnecessary to cultivate large numbers of different batches of samples as in the existing monitoring methods.

(4) Since a continuous constant flow cultivating scheme and a real-time detecting scheme are adopted and the experiment is performed fully automatically, an operator may operate remotely far away from a radiation source.

(5) A coincidence detection scheme is adopted. Sensitivity for different regions in a view field can be adjusted by adjusting a relative position of a detector or a cultivating dish. And different weights of sensitivity is given to the cultivating solution in an upper layer and cultivating cells in a lower layer, because the number of the radioactive labels taken by a cell in the lower layer is a focus of the experiment. In this way, a measuring result can be more accurate and apparent.

(6) A general cultivating instrument in the biomedical field is adopted as a carrier for an experiment object, which is convenient to be used by being coupled with other biochemical analysis instruments.

In the above, the multichannel in-vitro metabolism real-time monitoring apparatus according to the present disclosure is described in detail. Changes may be made to the embodiments and the application range by those skilled in the art according to the concept of the embodiments of the present disclosure. As summarized above, the content of the present specification should not be construed as limiting the present disclosure.

What is claimed is:

1. A multichannel in-vitro metabolism real-time monitoring apparatus for continuously cultivating in-vitro biological samples in a plurality of channels and monitoring metabolism information of the in-vitro biological sample in each of the plurality of channels, comprising a constant flow circulator and a radiation detector, wherein the constant flow circulator is provided with a multichannel biochemical cultivating instrument comprising a plurality of cultivating wells, and is configured to continuously cultivate biological samples in the plurality of channels of the multichannel biochemical cultivating instrument, wherein the plurality of channels is a plurality of cultivating dishes with a same specification on a same plate, and the plurality of cultivating dishes is arranged in array; and the radiation detector comprises two detecting modules respectively arranged on two sides of the multichannel biochemical cultivating instrument, wherein:

each of the two detecting modules includes a scintillation crystal, a photoelectric conversion component and a data processing transmitting module, and the two detecting modules are configured to perform a coincidence detection on the multichannel biochemical cultivating instrument, record the radioactivity for each of cultivating wells of the multichannel biochemical cultivating instrument in real time and continuously monitor a total number of metabolic substrates in each of the cultivating wells;

each of the two detecting modules has a flat-plate structure and comprises a plurality of dedicated detecting units corresponding to the cultivating wells in a one-to-one manner such that each of the cultivating wells corresponding to a couple of the dedicated detecting units respectively in the two detecting modules is located between the couple of the dedicated detecting units, wherein the couple of the dedicated detecting units are located at positions corresponding to each other for detecting a couple of gamma photons generated simultaneously in a decay with reversed emission directions, and a center of the dedicated detecting unit is aligned with a center of a circle of the cultivating well corresponding to the dedicated detecting unit, and a length of a side of the dedicated detecting unit is equal to a diameter of the cultivating well corresponding to the dedicated detecting unit.

2. The multichannel in-vitro metabolism real-time monitoring apparatus according to claim 1, wherein the constant flow circulator comprises a solution supply flask, a multichannel constant flow pump and a multichannel solution splitter, and the solution supply flask is configured to provide fresh cultivating solution containing a radioactive label;

the multichannel constant flow infusing pump configured to input and output cultivating solution containing a radioactive metabolic substrate to and from each of the plurality of channels of the multichannel biochemical cultivating instrument, to provide updated cultivating solution with a constant flow rate to a cultivated object; and the multichannel solution splitter is configured to equally distribute the cultivating solution to each of cultivating wells and collect waste solution from each of the cultivating wells with independent channels.

3. The multichannel in-vitro metabolism real-time monitoring apparatus according to claim 2, wherein the constant flow circulator further comprises a waste solution flask configured to collect the cultivating solution refluxed from the multichannel biochemical cultivating instrument after tissue in the multichannel biochemical cultivating instrument is cultivated and metabolized.

4. The multichannel in-vitro metabolism real-time monitoring apparatus according to claim 1, wherein the two detecting modules are completely the same and are opposite to each other.

5. The multichannel in-vitro metabolism real-time monitoring apparatus according to claim 1, wherein the dedicated detecting unit is changed based on different cultivating well specifications.

6. The multichannel in-vitro metabolism real-time monitoring apparatus according to claim 1, wherein each of the two detecting modules comprises a plurality of non-dedicated detecting units with constant sizes, the non-dedicated detecting unit with the constant size is formed by constant array detectors which are combined into a detecting unit with a same size as a used cultivating well in a subsequent data processing procedure.

7. The multichannel in-vitro metabolism real-time monitoring apparatus according to claim 1, further comprising a position adjustor configured to adjust relative positions between the two detecting modules and the multichannel biochemical cultivating instrument.

8. The multichannel in-vitro metabolism real-time monitoring apparatus according to claim 1, further comprising a data processor connected to the radiation detector, wherein the data processor is configured to package acquired detection information into a single event data frame and transmit the single event data frame to a host computer, to process and analyze the single event data frame with analysis software on the host computer.

9. The multichannel in-vitro metabolism real-time monitoring apparatus according to claim 8, wherein the analysis software is configured to: perform in real time a position coincidence and a time coincidence on a single gamma photon data frame received from two detecting modules with flat-plate structures, to obtain count information of a decay event for each of the plurality of channels of the multichannel biochemical cultivating instrument, to further obtain a time-count rate curve for each of the plurality of channels and to complete a data processing analyzing function.

10. The multichannel in-vitro metabolism real-time monitoring apparatus according to claim 1, wherein the multichannel biochemical cultivating instrument is a standardized instrument in a biomedical field.

11. The multichannel in-vitro metabolism real-time monitoring apparatus according to claim 1, wherein the plurality of channels of the multichannel biochemical cultivating instrument have a same specification, flow rates of cultivating solution respectively inputted to the plurality of channels are the same and concentrations of radioactive metabolic substrates in the cultivating solution respectively inputted to the plurality of channels are the same.

12. The multichannel in-vitro metabolism real-time monitoring apparatus according to claim 1, wherein the multichannel in-vitro metabolism real-time monitoring apparatus further comprising a computer, wherein the computer is configured to acquire the actual position at which the decay event occurs based on information of location and time of each of the couple of gamma photons, such that the activity information for different cultivating positions is obtained.

13. The multichannel in-vitro metabolism real-time monitoring apparatus according to claim 12, wherein the two detecting modules are completely the same and are opposite to each other.

14. The multichannel in-vitro metabolism real-time monitoring apparatus according to claim 12, wherein the computer is configured to acquire a position point on a detecting module at which each of the gamma photons enters, thereby acquiring a connection line; a position on the connection line at which the decay event occurs is determined based on information of a difference between times at which the two gamma photons arrive at the two detecting modules; an actual position at which the decay event occurs in a detecting region is acquired for each decay event, and the activity information for different cultivating positions is obtained.

15. The multichannel in-vitro metabolism real-time monitoring apparatus according to claim 1, wherein the multichannel in-vitro metabolism real-time monitoring apparatus further comprising a computer, wherein the computer is configured to obtain the activity information for a detecting region based on the lightness and the shade of the image acquired dynamically by the two detecting modules.

16. The multichannel in-vitro metabolism real-time monitoring apparatus according to claim 14, wherein the two detecting modules are served as front detectors of a PET.

17. The multichannel in-vitro metabolism real-time monitoring apparatus according to claim 14, wherein the computer is configured to divide the acquired image to a plurality of sub-regions corresponding to different cultivating positions, the activity information corresponding to each sub-region is obtained by calculating a sum of pixel values in the sub region.

18. The multichannel in-vitro metabolism real-time monitoring apparatus according to claim 17, wherein the computer is configured to divide the acquired image to sub regions based on a geometric size and a spatial position of the multichannel biochemical cultivating instrument.

\* \* \* \* \*